US009990606B2

(12) United States Patent
Hoffman

(10) Patent No.: US 9,990,606 B2
(45) Date of Patent: *Jun. 5, 2018

(54) SYSTEMS AND METHODS FOR MEASURING AND TRACKING RADIO-FREQUENCY IDENTIFICATION TAGS

(71) Applicant: George Kevin Hoffman, Mooresville, NC (US)

(72) Inventor: George Kevin Hoffman, Mooresville, NC (US)

(*) Notice: Subject to any disclaimer, the term of this patent is extended or adjusted under 35 U.S.C. 154(b) by 1 day.

This patent is subject to a terminal disclaimer.

(21) Appl. No.: 15/595,653

(22) Filed: May 15, 2017

(65) Prior Publication Data

US 2017/0316373 A1    Nov. 2, 2017

Related U.S. Application Data

(63) Continuation of application No. 14/324,694, filed on Jul. 7, 2014, now Pat. No. 9,652,733.
(Continued)

(51) Int. Cl.
   *G06F 11/34* (2006.01)
   *G06Q 10/08* (2012.01)
   (Continued)

(52) U.S. Cl.
   CPC ....... *G06Q 10/087* (2013.01); *G06F 11/3409* (2013.01); *G06K 7/0008* (2013.01);
   (Continued)

(58) Field of Classification Search
   CPC .......... G01N 2035/00762; G01N 2035/00811; G01N 2035/00821; G01N 2035/0091;
   (Continued)

(56) References Cited

U.S. PATENT DOCUMENTS 5,324,922 A    6/1994 Roberts
7,154,283 B1   12/2006 Weakley et al.
(Continued)

FOREIGN PATENT DOCUMENTS

JP    2008176633 A1   7/2008
WO    2006031824 A2   3/2006

OTHER PUBLICATIONS

Maloni, M., et al., "Understanding Radio Frequency Identification (RFID) and Its Impact on the Supply Chain," Jul. 26, 2006, pp. 1-44.
International Search Report and Written Opinion for PCT/US2014/045570 dated Dec. 17, 2014 (16 pp.).
Extended European Search Report for European Patent Application No. 14822380.3 dated Oct. 31, 2016. (9 pages).

*Primary Examiner* — Dionne H Pendleton
(74) *Attorney, Agent, or Firm* — Neal, Gerber & Eisenberg LLP

(57) ABSTRACT

Systems and methods are provided for measuring and tracking radio-frequency (RFID) tags. Inlay data, converting data, and tag scan data can be received from entities in the supply chain and stored in a database. The tag scan data, including measurement and performance data, can be stored and used for applications such as determining whether RFID tags are defective. The tag scan data, inlay data, and converting data can be analyzed to produce analytic data for reporting and failure prediction purposes. Inlay-SKU combinations of RFID tags can be validated to ensure that the correct inlays are being utilized for RFID tags intended for particular products. More accurate inventory data may be obtained and costs for re-tagging products that have defective RFID tags may be reduced. Entities in the supply chain can also be assisted to comply with various quality control, licensing, and tracking requirements related to the RFID tags.

22 Claims, 8 Drawing Sheets

Related U.S. Application Data

(60) Provisional application No. 61/911,766, filed on Dec. 4, 2013, provisional application No. 61/844,791, filed on Jul. 10, 2013.

(51) Int. Cl.
*G06K 7/00* (2006.01)
*G06K 19/07* (2006.01)
*G01N 35/00* (2006.01)
*G06K 7/10* (2006.01)

(52) U.S. Cl.
CPC ....... *G06K 7/0095* (2013.01); *G06K 19/0723* (2013.01); *G01N 2035/00772* (2013.01); *G06K 7/10465* (2013.01)

(58) Field of Classification Search
CPC ....... G01N 35/00584; G01N 35/00663; G01N 35/00732; G01N 35/0099; G01N 35/04; G01N 2035/00435; G01N 2035/00673; G06F 17/00; G06F 3/002; G07F 17/3225; G07F 17/3244; G07F 7/00; G07G 1/00; H04N 1/00342; H04N 1/32138; H04N 2201/0081; Y10T 436/11; Y10T 436/13; G06Q 10/087; G06Q 30/018; G06Q 30/0185; G06Q 30/0623; G06K 7/10217; G06K 7/10366; G06K 7/10435; G06K 7/10465; G06K 2017/0041; G06K 2017/0067; G06K 7/0095; G06K 7/10039; G06K 7/10089; G06K 7/10168
See application file for complete search history.

(56) References Cited

U.S. PATENT DOCUMENTS

| | | |
|---|---|---|
| 7,164,353 B2 | 1/2007 | Puleston et al. |
| 7,295,117 B2 | 11/2007 | Forster et al. |
| 7,411,498 B2 | 8/2008 | Forster |
| 7,570,165 B2 | 8/2009 | Abraham, Jr. et al. |
| 7,659,822 B2 | 2/2010 | Carrender et al. |
| 7,827,200 B2 | 11/2010 | Rowe et al. |
| 8,006,904 B2 | 8/2011 | Salim et al. |
| 8,421,600 B2 | 4/2013 | Erickson et al. |
| 8,472,046 B2 | 6/2013 | Hoffman et al. |
| 9,652,733 B2 * | 5/2017 | Hoffman .............. G06Q 10/087 |
| 2006/0082444 A1 | 4/2006 | Sweeney et al. |
| 2006/0261954 A1 | 11/2006 | Dietrich et al. |
| 2006/0290502 A1 | 12/2006 | Rawlings |
| 2007/0200686 A1 | 8/2007 | Jung |
| 2007/0296554 A1 | 12/2007 | Marcus et al. |
| 2008/0258916 A1 | 10/2008 | Diorio et al. |
| 2009/0167502 A1 | 7/2009 | Erickson et al. |
| 2010/0188244 A1 | 7/2010 | Sattler |
| 2010/0283584 A1 | 11/2010 | McAllister |
| 2010/0289627 A1 | 11/2010 | McAllister et al. |
| 2010/0324722 A1 | 12/2010 | Fritchie |
| 2011/0050400 A1 | 3/2011 | Ho et al. |
| 2012/0274448 A1 | 11/2012 | Marcus et al. |
| 2012/0282998 A1 | 11/2012 | Emori |
| 2013/0048711 A1 | 2/2013 | Burns et al. |
| 2013/0168454 A1 | 7/2013 | Oh |
| 2016/0140820 A1 | 5/2016 | Joseph |

\* cited by examiner

SYSTEMS AND METHODS FOR MEASURING AND TRACKING RADIO-FREQUENCY IDENTIFICATION TAGS

CROSS-REFERENCE TO RELATED APPLICATIONS

This application is a continuation of U.S. Non-Provisional patent application Ser. No. 14/324,694, filed Jul. 7, 2014, which claims priority to U.S. Provisional Patent Application Ser. No. 61/844,791, filed on Jul. 10, 2013, and U.S. Provisional Patent Application Ser. No. 61/911,766, filed on Dec. 4, 2013, all of which are incorporated herein by reference.

TECHNICAL FIELD

This invention relates to systems and methods for measuring, evaluating, and tracking radio-frequency identification (RFID) tags. More particularly, the invention provides systems and methods for collecting data related to the performance characteristics of RFID tags across a supply chain and the quality of data encoded within the RFID tags, analyzing the data to identify and predict defective RFID tags within the supply chain, storing the data to ensure quality control metrics are met, validating inlay-SKU combinations of RFID tags within the supply chain, and performing auditing and compliance of inlays and/or RFID chips in RFID tags with respect to licensing agreements.

BACKGROUND OF THE INVENTION

Many companies, such as retailers and manufacturers, utilize RFID tags to uniquely identify products for purposes such as inventory control and optimizing product availability. RFID tags are typically attached to products to enable the companies to wirelessly detect the presence of the products. For example, mobile or fixed scanners can be utilized by employees to quickly and easily determine inventory in a retail store. By using this information, the companies can determine if the amount of inventory is sufficient and/or whether certain products need to be replenished.

A typical RFID tag is encoded with an SGTIN (Serialized Global Trade Item Number) that is a universal identifier for uniquely identifying a particular physical object, e.g., a product. The SGTIN can be associated not only with the particular object, but also with a distinct category or family of objects all having the same SKU (stock keeping unit). For example, an apparel product of a certain style, size, and color (e.g., mini, size 8, red, dress) may have a particular SKU. Each of the products may share the same SKU but have a unique SGTIN that is a combination of the SKU and a unique identifier. Accordingly, the precise number of products can be determined by scanning the RFID tags attached to the products and counting the unique SGTINs for a particular SKU. In addition to inventory control, SGTINs may be used for other purposes, such as to help detect counterfeit products or prevent diversion of authentic products. All of these applications require the successful reading of the RFID tag throughout a supply chain.

However, RFID tags can degrade or become defective. When RFID tags degrade or become defective, they may be unable to be read by scanners in a reliable and consistent fashion. In particular, RFID tags could degrade to different levels of degradation that may cause scanners to incorrectly read the RFID tags, not read the RFID tags, and/or make the RFID tags unreadable from a required distance, for example. The inability to read RFID tags can adversely impact the effectiveness of RFID-based applications. For example, when RFID tag failure occurs, the inventory count of products in a retail store can be inaccurate. This may result in the false appearance of insufficient inventory, the improper replenishing of products that do not need to be replenished, and/or the need to re-tag products after the products have been delivered to a retail store. RFID tags can degrade or become defective due to physical damage (e.g., folding, creasing, impacts, etc.), electrostatic discharge, temperature, humidity, and/or other causes. In particular, components of RFID tags, such as RFID chips, antennas, and/or inlays, can degrade or become defective. Some studies have shown that a significant number of RFID tags can degrade or become defective as the components and the completed RFID tags themselves move through a supply chain. The supply chain can be complex and involve many different entities that require conveying the components and the RFID tags between the entities. As such, there are many potential points in the supply chain where RFID degradation or tag failure could be caused.

RFID tags can also be considered defective if the data encoded within the RFID tags is incorrect. In one aspect, RFID tags encoded with duplicate SGTINs have incorrect data and can be considered defective. In particular, if the SGTIN encoded in a particular RFID tag is the same as the SGTIN encoded in one or more other RFID tags, all of the RFID tags with the same SGTIN can be considered defective. Products that have such RFID tags attached would not be counted correctly, resulting in incorrect inventory counts. For example, a scanner would only count one product when RFID tags with the same SGTIN are scanned because only one SGTIN would be detected.

In another aspect, RFID tags encoded with SGTINs that do not conform to a required encoding scheme have incorrect data and can be considered defective. The required encoding scheme may be established by a retailer, for example, and can include rules or protocols that specify how the SGTIN must be encoded. One goal of such encoding schemes may be to minimize the possibility of encoding duplicate SGTINs in multiple RFID tags. The encoding scheme can include, for example, Multi-vendor Chip Serialization (MCS) from GS1 and proprietary encoding schemes. However, if the encoding scheme is not followed correctly when the SGTIN is created, duplicate SGTINs and/or SGTINs that do not conform to the encoding scheme can result. Duplicate and incorrectly encoded SGTINs can also result in incorrect inventory counts of products.

Another problem associated with RFID tags relates to the use of wrong inlays within an RFID tag. An inlay in an RFID tag consists of an RFID chip attached to an antenna. A company may require that an RFID tag for a particular product (and SKU) includes a particular combination of a specific RFID chip and a specific antenna. This particular combination may be required to improve read rates of the RFID tags when attached to these particular products. For example, a particular inlay may be required so that it can be read from a farther distance, e.g., due to a larger antenna in the inlay. Existing RFID printers and scanners can only read the TID (Tag Identification Number) of the RFID chip in an inlay and cannot detect the type of antenna that is in the inlay. As such, it is possible that an RFID tag printer/converter, by accident or with intent (e.g., use of a lower cost underperforming inlay), could use the wrong type of inlay, e.g., with the correct RFID chip but the wrong antenna type, when producing an RFID tag for a particular product (with a particular SKU).

Additional issues associated with RFID tags relate to the licensing of inlays and/or RFID chips within the RFID tags. Entities that produce inlays and/or RFID chips may or may not be a party to a license agreement. Auditors, compliance entities, and other users may wish to determine if particular inlays and/or RFID chips are compliant with the license agreement for auditing and compliance purposes. However, merely scanning an RFID tag does not reveal enough information to determine whether the particular inlay and/or RFID chip in the RFID tag is compliant with the license agreement.

Therefore, there exists an opportunity for systems and methods for collecting data related to the performance characteristics of RFID tags across a supply chain and the quality of data encoded within the RFID tags, analyzing the data to identify and predict defective RFID tags within the supply chain, storing the data to ensure quality control metrics are met, validating inlay-SKU combinations of RFID tags within the supply chain, and performing auditing and compliance of inlays and/or RFID chips in RFID tags with respect to licensing agreements.

SUMMARY OF THE INVENTION

The invention is intended to solve the above-noted problems by providing systems and methods for collecting data related to the performance characteristics of RFID tags across a supply chain, analyzing the data to identify and predict RFID tag failures within the supply chain, and validating inlay-SKU combinations of RFID tags within the supply chain. The systems and methods are designed to, among other things: (1) receive and/or store inlay data and converting data; (2) receive tag scan data related to RFID tags, including measurement data and performance data, from an entity in a supply chain; (3) determine whether the tag scan data denotes a particular RFID tag is defective, including whether the RFID tag has a duplicate SGTIN and/or whether an SGTIN in the RFID tag complies with an encoding scheme; (4) flag the particular RFID tag as defective in an RFID tag data database; (5) store the tag scan data in the RFID tag data database regardless of whether an RFID tag is defective; (6) analyze the tag scan data, inlay data, and converting data to produce analytic data; (7) predict failures of RFID tags based on the analytic data; (8) determine whether particular inlay-SKU combinations of an RFID tag in a supply chain are valid; and (9) perform auditing and compliance of inlays and/or RFID chips in RFID tags with respect to licensing agreements.

In a particular embodiment, a plurality of RFID tags can be measured. Inlay data related to the plurality of RFID tags can be received, and converting data related to the plurality of RFID tags can be received. Tag scan data related to at least one RFID tag of the plurality of RFID tags can also be received. The tag scan data may include a unique identifier of the at least one RFID tag. It can be determined whether the tag scan data denotes that the at least one RFID tag is defective, based on one or more of the tag scan data, the inlay data, or the converting data. If the tag scan data denotes that the at least one RFID tag is defective, then the at least one RFID tag can be flagged as defective in the RFID tag data database, such as by storing the unique identifier of the at least one RFID tag in an RFID tag data database.

In another embodiment, a plurality of RFID tags can be measured. Inlay data related to the plurality of RFID tags can be received, and converting data related to the plurality of RFID tags can be received. Tag scan data related to at least one MID tag of the plurality of REED tags can also be received. The tag scan data may include a unique identifier of the at least one RFID tag. The level of degradation of the at least one RFID tag can be determined, based on one or more of the tag scan data, the inlay data, or the converting data. The level of degradation of the at least one RFID tag can be stored in the RFID tag data database.

In a further embodiment, a plurality of RFID tags can be measured, inlay data related to the plurality of RFID tags can be received, and converting data related to the plurality of RFID tags can be received. Tag scan data related to at least one RFID tag of the plurality of RFID tags can also be received. The tag scan data may include a unique identifier of the at least one RFID tag. Analytic data can be produced based on one or more of the tag scan data, the inlay data, or the converting data. The analytic data can be transmitted.

These and other embodiments, and various permutations and aspects, will become apparent and be more fully understood from the following detailed description and accompanying drawings, which set forth illustrative embodiments that are indicative of the various ways in which the principles of the invention may be employed.

DETAILED DESCRIPTION OF THE INVENTION

Figure 1:
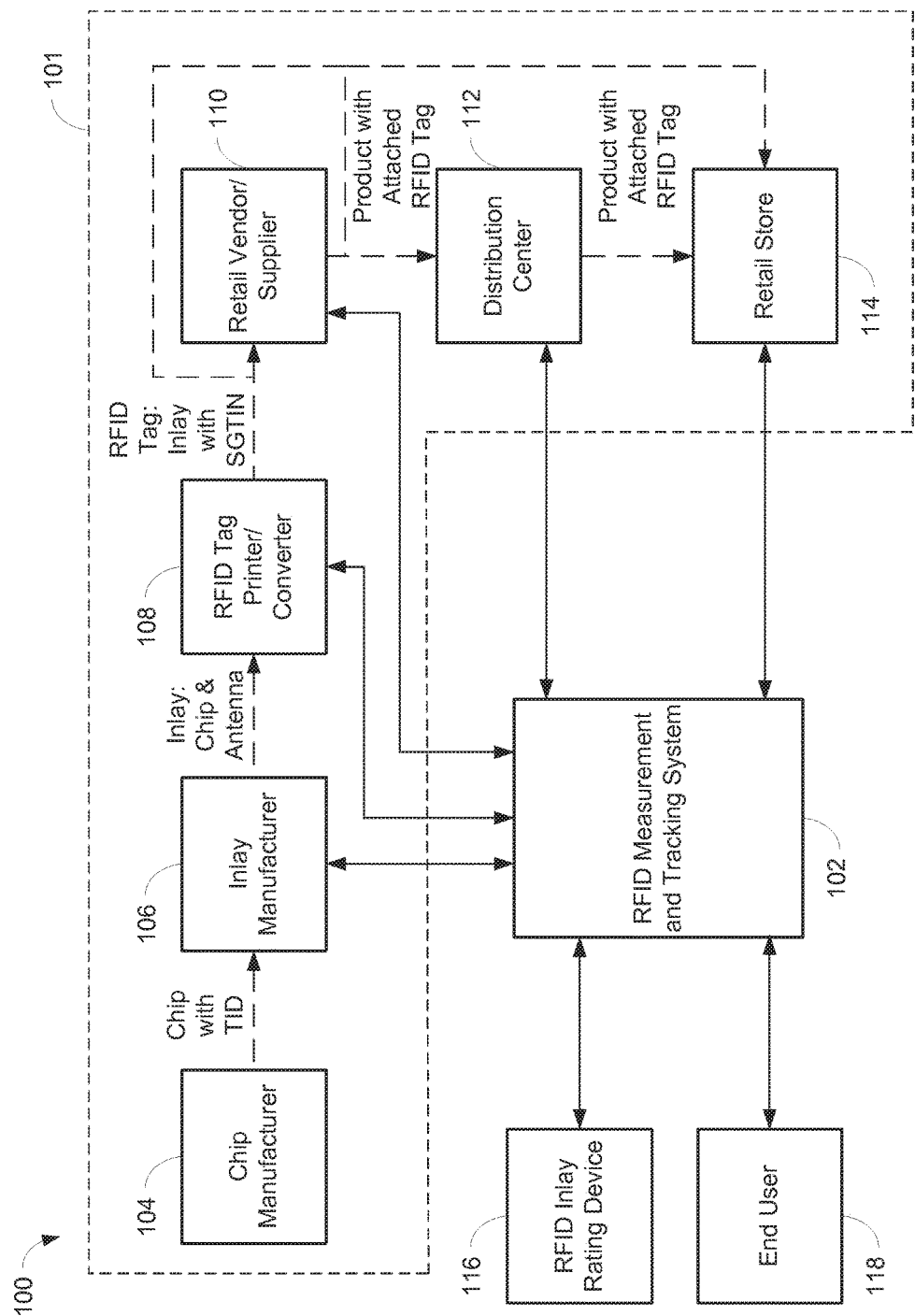
FIG. 1 is a block diagram illustrating a supply chain and a system for measuring and tracking RFID tag performance across the supply chain.

The description that follows describes, illustrates and exemplifies one or more particular embodiments of the invention in accordance with its principles. This description is not provided to limit the invention to the embodiments described herein, but rather to explain and teach the principles of the invention in such a way to enable one of ordinary skill in the art to understand these principles and, with that understanding, be able to apply them to practice not only the embodiments described herein, but also other embodiments that may come to mind in accordance with these principles. The scope of the invention is intended to cover all such embodiments that may fall within the scope of the appended claims, either literally or under the doctrine of equivalents.

It should be noted that in the description and drawings, like or substantially similar elements may be labeled with the same reference numerals. However, sometimes these elements may be labeled with differing numbers, such as, for example, in cases where such labeling facilitates a more clear description. Additionally, the drawings set forth herein are not necessarily drawn to scale, and in some instances proportions may have been exaggerated to more clearly depict certain features. Such labeling and drawing practices do not necessarily implicate an underlying substantive purpose. As stated above, the specification is intended to be taken as a whole and interpreted in accordance with the principles of the invention as taught herein and understood to one of ordinary skill in the art.

FIG. 1 illustrates a system 100 including a supply chain 101 in communication with an RFID measurement and tracking system 102 for collecting data related to the performance characteristics of RFID tags across the supply chain 101 and the quality of data encoded within the RFID tags, analyzing the data to identify and predict defective RFID tags within the supply chain 101, storing the data to ensure quality control metrics are met, validating inlay-SKU combinations of RFID tags within the supply chain 101, and performing auditing and compliance of inlays in RFID tags with respect to licensing agreements, in accordance with one or more principles of the invention. The supply chain 101 and the RFID measurement and tracking system 102 of the system 100 can be in separate physical locations or in the same physical locations. In addition, the entities included in the supply chain 101 may be in separate physical locations or in some or all of the same physical locations. By utilizing the RFID measurement and tracking system 102 in conjunction with the supply chain 101, defective RFID tags may be detected earlier in the supply chain 101 and root causes for the defective RFID tags may be identified. This information can be utilized to improve processes in the entities of the supply chain 101 to reduce the occurrence of defective RFID tags. As a result, inventory data may be more accurate and costs for re-tagging products that have defective RFID tags may be reduced. In addition, use of the RFID measurement and tracking system 102 can assist entities in the supply chain 101 to comply with various quality control, licensing, and tracking requirements related to the RFID tags.

The supply chain 101 related to the RFID tags may include a chip manufacturer 104, an inlay manufacturer 106, an RFID tag printer/converter 108, a retail vendor/supplier 110, a distribution center 112, and/or a retail store 114. Components of the RFID tags and the RFID tags themselves can be manufactured and distributed using the supply chain 101 so that ultimately products with attached RFID tags are present at the retail store 114. It should be noted that the dotted lines between the entities of the supply chain 101 in FIG. 1 denote the physical conveyance of an item (e.g., a component of an RFID tag, an RFID tag itself, or a product with an attached RFID tag). The conveyance may be performed by a carrier or other appropriate transport.

As an initial step in producing an RFID tag in the supply chain 101, a chip manufacturer 104 may manufacture an RFID chip that is permanently encoded with a Tag Identification Number (TID). The TID is read-only, cannot be modified, and is a permanent part of the RFID tag that the RFID chip will be included in. The produced RFID chip with TID can be conveyed from the chip manufacturer 104 to an inlay manufacturer 106. The inlay manufacturer 106 may attach the RFID chip to an antenna to produce an inlay. A particular type of RFID chip can be attached to different types of antennas depending on the requirements of a retailer and/or the desired performance of an RFID tag, e.g., greater read distance. The inlays may be produced in rolls as dry inlays, wet inlays, or paper faced inlays, as is known in the art. The produced inlays can be conveyed from the inlay manufacturer 106 to the RFID tag printer/converter 108.

The RFID tag printer/converter 108 typically receives inlays on rolls and produces finished RFID tags that include the inlays. For example, a dry inlay may be sandwiched between two pieces of paper stock to create a finished RFID tag that conceals the inlay. A wet inlay may be adhered to one side of a piece of paper stock to create a finished RFID tag. Paper faced inlays can be directly printed on with a printer/encoder so that human-readable content is printed on the finished RFID tag. Regardless of the type of inlay, the RFID tag printer/converter 108 also encodes a SGTIN (Serialized Global Trade Item Number) into the RFID chip in the finished RFID tag. The SGTIN typically includes a combination of a SKU (stock keeping unit) for a particular product and a unique identifier, such as a serial number. In some embodiments, the unique identifier can be assigned, and in other embodiments, the unique identifier can be derived using an algorithm based upon the TID of the RFID chip. The format of the SGTIN, e.g., the relationship between a SKU and a particular product, may be specified by a retail vendor/supplier 110 and may conform to certain standards, such as those developed by GS1 and/or proprietary standards. The finished RFID tag can be conveyed from the RFID tag printer/converter 108 to the retail vendor/supplier 110 for attachment to products. In some embodiments, the finished RFID tag can be conveyed from the RFID tag printer/converter 108 to a retail store 114. In this case, the retail store 114 can attach the RFID tags to the products.

The retail vendor/supplier 110 includes companies that manufacture and provide products to retailers that typically operate the retail stores 114. The products manufactured and provided by the retail vendor/supplier 110 can include consumer products (e.g., apparel, cosmetics, electronics, perishable items, etc.), business products, industrial products, and other types of products. The retail vendor/supplier 110 can attach the finished RFID tags to the products, in addition to attaching price tags and other markings to the products. For example, a shirt manufacturer in Asia may be the retail vendor/supplier 110 for an American retailer that has a distribution center 112 and/or retail store 114 in the United States. The RFID tags may be conveyed to the shirt manufacturer so that after shirts are produced, the shirt manufacturer can attach the RFID tags to the shirts prior to their shipment to the United States.

The manufactured products with the attached RFID tags can be conveyed from the retail vendor/supplier 110 to a distribution center 112, or in some embodiments, to the retail store 114. The distribution centers 112 are typically located regionally so that products can be received from the retail vendor/supplier 110 and then distributed to individual retail stores 114. Regardless of whether the products are conveyed to the retail store 114 from the retail vendor/supplier 110 or the distribution center 112, the products with the attached RFID tags are received and typically stored initially in a stockroom or backroom of the retail store 114. The products may then be placed on shelves or otherwise made available for transactions at the retail store 114.

The RFID tags and/or the RFID chips within the RFID tags may be scanned and read at any point in the supply chain 101 so that tag scan data can be transmitted to and collected by the RFID measurement and tracking system 102. The tag scan data may include measurement data and/or performance data related to the RFID tags and/or the RFID chips within the RFID tags. The measurement data and performance data may indicate whether RFID tags and chips are readable or unreadable, and/or a level of degradation of RFID tags and chips. The TID of the RFID chips may be read at any of the entities in the supply chain 101, but the SGTIN may be read at the tag printer/converter 108, the retail vendor/supplier 110, the distribution center 112, and/or the retail store 114. In particular, at the inlay manufacturer 106, the RFID chips can be scanned before, during, and after production of an inlay to test for readability of the TID of the RFID chips, and to measure properties of the RFID chips, e.g., attenuation. The RFID tags may be read by mobile scanners, interrogators, and/or other types of RFID tag readers, as is known in the art, and the tag scan data may be transmitted from the particular entity in the supply chain 101 to the RFID measurement and tracking system 102. In some embodiments, the RFID tags may be read by other scanning devices, such as the RFID inlay rating device 116 described below, that can obtain tag scan data and also measure and/or detect performance characteristics of the RFID tags, chips, and/or inlays. Such tag scan data may be transmitted via a public network, such as the Internet, and/or through other types of networks. The tag scan data can be utilized by the RFID measurement and tracking system 102 to measure and track the performance of the scanned RFID tags, such as to determine defective RFID tags and to flag such defective RFID tags in a database. Analysis of the tag scan data may be performed in conjunction with other data to produce analytic data that can assist an end user 118, e.g., retailer personnel, to determine causes of defective RFID tags. The analytic data can also be used to predict the failure of future RFID tags in the supply chain 101 and allow personnel to take corrective actions to reduce the number of defective RFID tags in the supply chain 101. The analytic data can further be used for auditing and compliance purposes related to a license agreement. Further details of the RFID measurement and tracking system 102 are described below in conjunction with FIG. 2.

An RFID inlay rating device 116 can also be in communication with the RFID measurement and tracking system 102 to read and rate the performance of an inlay in a RFID tag and transmit such performance data to the system 102. Properties of the RFID tag and/or inlay can be measured using the RFID inlay rating device 116. In particular, the RFID inlay rating device 116 may be in communication with an RFID tag scan data collection module 202, as described below. The RFID inlay rating device 116 can be mobile or fixed, and be utilized at any point in the supply chain 101 to obtain performance data about inlays in RFID tags. The RFID inlay rating device 116 may also be in communication with the RFID measurement and tracking system 102 to receive data from the system 102 for storage and/or display on the device 116.

When used for measuring properties of an RFID tag and/or inlay, the RFID inlay rating device 116 can collect and transmit tag scan data and/or performance data immediately to the RFID measurement and tracking system 102, and/or can collect and later upload the tag scan data and/or the performance data to the RFID measurement and tracking system 102. The performance data can include the SGTIN of the inlay, attenuation data (i.e., loss of signal strength of the RFID chip), and other information. In embodiments, the performance data can be utilized to identify failure patterns and any correlations between RFID tag problems and the performance data. For example, a user (e.g., the end user 118) can use the RFID inlay rating device 116 to detect a large number of RFID tags that are not readable or are being read at less than the desired distance. The performance data obtained from the RFID inlay rating device 116 can then be used to determine if any of these RFID tags had common performance criteria, e.g., high attenuation, that contributed to their failures. In this way, RFID tags and/or inlays (and their performance characteristics) can be graded, in contrast to existing RFID scanners which typically can only read or not read an RFID tag. RFID tags that are graded lower may have a lesser chance of being accurately read by different RFID scanners, and conversely, RFID tags that are graded higher may have a greater chance of being accurately read by different RFID scanners.

The RFID inlay rating device 116 can also receive data from the RFID measurement and tracking system 102 in real-time and/or on a delayed basis. The data may include information related to scanned RFID tags and/or inlays, and may be stored and/or displayed on the RFID inlay rating device 116. As an example, an RFID tag can be scanned by the RFID inlay rating device 116 to obtain performance data. The performance data can be transmitted to the system 102 for storage in a database, such as an RFID tag data database 208 and/or inlay data database 212. The system 102 can determine whether an RFID tag has a valid inlay-SKU combination, determine whether an inlay in an RFID tag is properly licensed, detect a duplicate SGTIN in multiple RFID tags, verify compliance of an SGTIN with an encoding scheme, and/or perform other functions based on the performance data. Embodiments of such functions of the system 102 are described in more detail below. The RFID inlay rating device 116 can receive data from the system 102, such as information specifying that the RFID tag has a valid or invalid inlay-SKU combination, that the inlay in the RFID tag is properly licensed, that an SGTIN in an RFID tag complies with an encoding scheme, and/or that an RFID tag has a duplicate SGTIN. The RFID inlay rating device 116 can store the information in memory and/or display the information to a user.

In some embodiments, the RFID inlay rating device 116 may be implemented as a software application executing on a computing device, such as a smartphone. For example, a software application that implements the RFID inlay rating device 116 may execute on an electronic device that is in communication with an appropriate hardware device, e.g., a UHF scanner, for scanning RFID tags and/or inlays. The device may be integral or peripheral to the electronic device. Such a device may be in wired or wireless communication with the electronic device for power and/or data transfer purposes. For example, a UHF scanner may physically interface with the audio jack of a smartphone, or may wirelessly connect to a smartphone via a Bluetooth connection. The device can scan the RFID tags and/or inlays and transmit the obtained performance data to the software application. The software application may then transmit the performance data to the system 102, and/or receive data back from the system 102.

Figure 2:
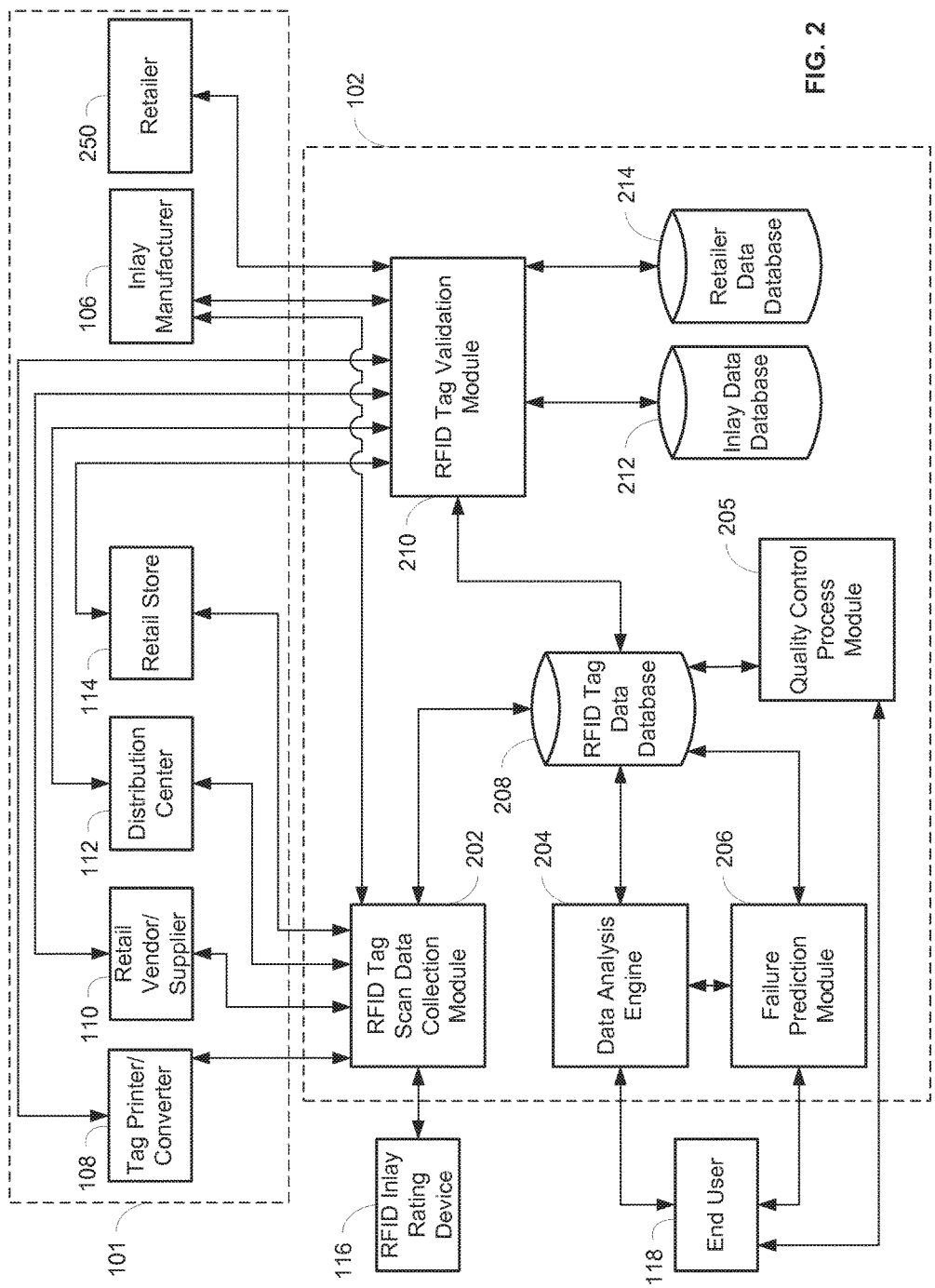
FIG. 2 is a block diagram illustrating the system for measuring and tracking RFID tag performance across the supply chain.
Figure 3:
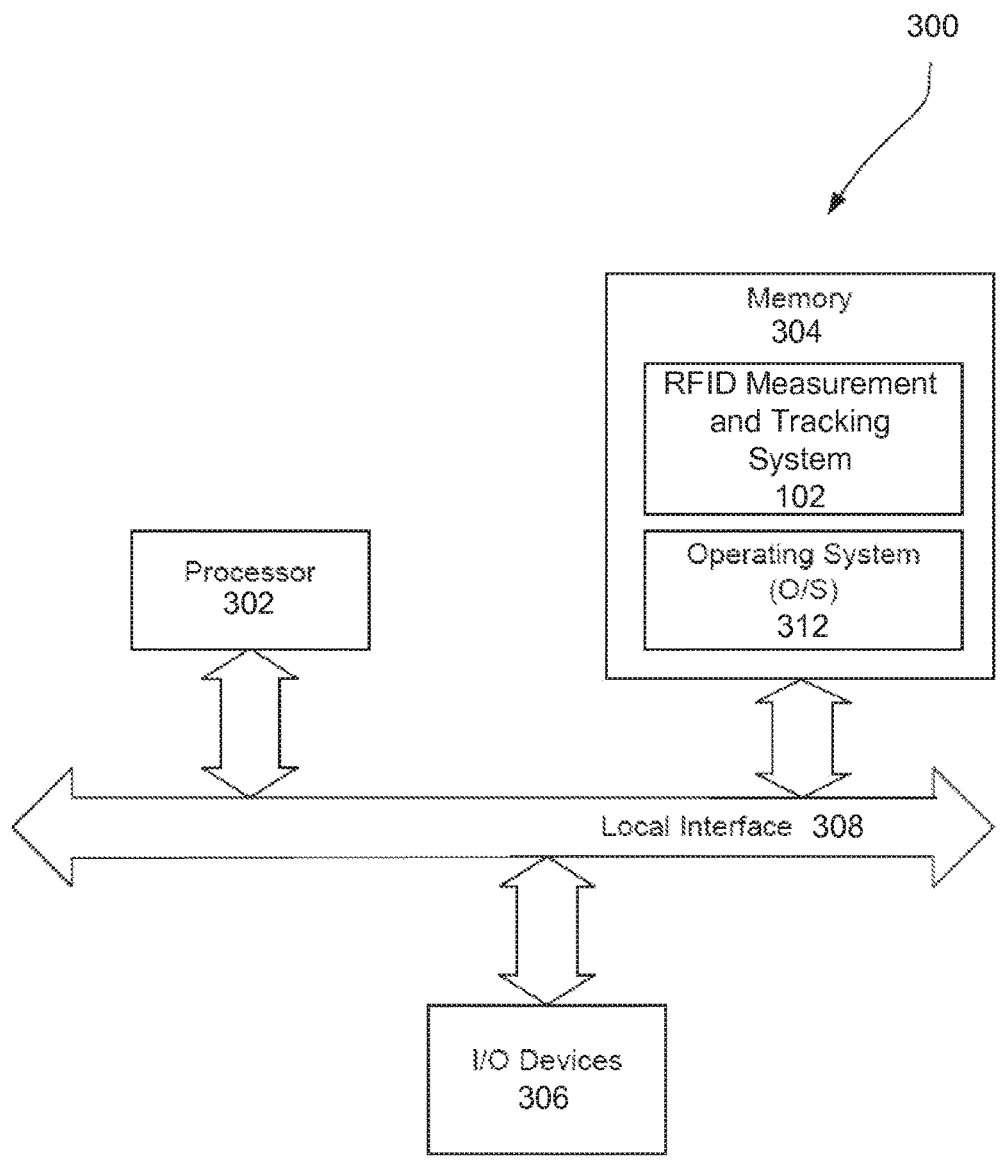
FIG. 3 is a block diagram of one form of a computer or server, having a memory element with a computer readable medium for implementing the system for measuring and tracking RFID tag performance across the supply chain.

FIG. 2 illustrates the RFID measurement and tracking system 102 of FIG. 1 and its communications with the entities of the supply chain 101, the RFID inlay rating device 116, and the end user 118. As described above, the RFID measurement and tracking system 102 can collect data related to RFID tags across the supply chain 101, analyze the data to identify and predict defective RFID tags within the supply chain 101, validate inlay-SKU combinations of RFID tags within the supply chain 101, and perform auditing and compliance of inlays in RFID tags with respect to licensing agreements, in accordance with one or more principles of the invention. Various components of the RFID measurement and tracking system 102 may be implemented using software executable by one or more servers or computers, such as a computing device 300 with a processor 302 and memory 304 as shown in FIG. 3, which is described in more detail below.

An RFID tag scan data collection module 202 can be in communication with entities in the supply chain 101 to collect inlay data of inlays, converting data of finished RFID tags, and tag scan data of scanned RFID tags. The inlay manufacturer 106 may transmit inlay data to the RFID tag scan data collection module 202 after an inlay is produced, such as a manufacture date, lot number, antenna type, inlay model number, quality control test results, the TID of the RFID chip in the RFID tag, and/or other data. The converting data may be transmitted by the tag printer/converter 108 to the RFID tag scan data collection module 202 after an RFID tag is finished, and can include a date and/or timestamp when the RFID tag was encoded, an order number, vendor(s) the RFID tag was shipped to, and/or other information. As RFID tags are conveyed between and to the tag printer/converter 108, retail vendor/supplier 110, distribution center 112, and/or retail store 114, the RFID tags may be scanned to obtain tag scan data. The tag scan data related to the scanned RFID tags can be transmitted to the RFID tag scan data collection module 202 from the entities in the supply chain 101. The tag scan data may include the SGTIN of an RFID tag, the TID of the RFID chip in the RFID tag, a tag grade, a date and/or timestamp when the RFID tag was scanned, a location of the scan, a user who performed the scan, performance data, and/or other information. The SKU of a product may be derived from the SGTIN of the RFID tag in the tag scan data. The inlay data, converting data, and/or tag scan data may be stored by the RFID tag scan data collection module 202 in an RFID tag data database 208.

In some embodiments, the inlay data and/or converting data may be transmitted from the inlay manufacturer 106 and/or the tag printer/converter 108, respectively, in response to queries by the RFID tag scan data collection module 202, in addition to or instead of storing the inlay data and/or converting data in the RFID tag data database 208. The inlay data and/or converting data may be retrieved on an as-needed basis for use by the data analysis engine 204, failure prediction module 206, quality control process module 205, and/or RFID tag validation module 210, as described below. For example, after receiving tag scan data, the RFID tag scan data collection module 202 may transmit a query to the inlay manufacturer 106 and/or the tag printer/converter 108 with information in the tag scan data, such as the TID of the RFID chip in the scanned RFID tag. In response to the query, the inlay manufacturer 106 and/or the tag printer/converter 108 may transmit the inlay data and/or converting data, based on the information in the tag scan data. For example, the TID in such a query can be used by the inlay manufacturer 106 to retrieve the inlay data from an internal database and transmit the inlay data to the RFID tag scan data collection module 202.

As tag scan data is collected, the RFID tag scan data collection module 202 can store the tag scan data to ensure quality control metrics are met and/or to determine whether a particular RFID tag is defective based on the tag scan data. If an RFID tag is determined as defective, the RFID tag may be flagged as defective in the RFID tag data database 208, along with other information, such as a timestamp, the SGTIN of the RFID tag, geoposition where the scan took place, an identifier of the device which was used to scan the RFID tag, an operator name, and/or other information. In one embodiment, an RFID tag can be determined as defective if a secondary printed barcode is scanned or manually entered as the tag scan data, for example, instead of receiving an RFID scanned SGTIN. The fact that a barcode was read would indicate to the RFID tag scan data collection module 202 that the RFID scan failed and that it was necessary to read the secondary barcode. The secondary barcode can have a Code 128 symbology, for example, be human-readable, and correspond to the SGTIN of the defective RFID tag.

In another embodiment, RFID tags can be determined as defective if the tag scan data indicates that the RFID tags have the same SGTIN. The tag scan data may include an SGTIN and a TID scanned from multiple RFID tags. If the TIDs from the multiple RFID tags are different but the SGTINs from the multiple RFID tags are the same, then the multiple RFID tags can be flagged as defective. Each of the multiple RFID tags should have a unique SGTIN, so the presence of the same SGTIN in the multiple RFID tags indicates that the RFID tags were not encoded correctly. In a further embodiment, an RFID tag can be determined as defective if the tag scan data indicates that the SGTIN encoded in the RFID tag does not conform to a specified encoding scheme. The encoding scheme can specify a format of the SGTIN based on a stock keeping unit (SKU) and a serial number, and may be proprietary for a particular retailer, for example, or may be standardized. If the SGTIN for an RFID tag does not conform to the encoding scheme, then the RFID tag was not encoded correctly. Duplicate and/or incorrectly encoded SGTINs can result in the incorrect inventory count of products to which the defective RFID tags are attached to.

The inlay data, the converting data, and/or the tag scan data in the RFID tag data database 208 may also be utilized by a data analysis engine 204 to produce analytic data related to the RFID tags. The analytic data may be utilized by an end user 118 to determine the causes of RFID tag failure and/or defective RFID tags. The end user 118 may be able to access the analytic data and/or the RFID tag data database 208 to view and assess the history of the RFID tags and reports including the analytic data. In one embodiment, an end user 118 may determine correlations between failures of an RFID tag and information corresponding to the defective RFID tag, such as a particular lot number of the inlay, a particular tag printer/converter 108, a particular retail vendor/supplier 110 that attached the RFID tag to the product, inlay grading information, and/or other information. For example, if a particular entity in the supply chain detects a duplicate SGTIN in multiple RFID tags, then it is likely that a previous entity in the supply chain has incorrectly encoded the SGTINs in the RFID tags. The analysis performed by the data analysis engine 204 may be based on none, some, or all of the inlay data; none, some, or all of the converting data; and/or none, some, or all of the tag scan data. The data analysis engine 204 may generate and provide the analytic data as reports in a text format, XML format, HTML format, and/or other appropriate format, for example.

A quality control process module 205 may be utilized to ensure that entities in the supply chain 101 are complying with the quality control requirements of a retailer or other specifier. For example, a retailer may establish a goal for their RFID tags to have 98% of the RFID tags to be readable with a 98% confidence level. To meet this target, the retailer may mandate that the tag printer/converter 108 should test 10% of the finished RFID tags prior to shipping to the retail vendor/supplier 110, and the retail vendor/supplier 110 should test 4% of the RFID tags upon receipt of the RFID tags and then test 2% of the RFID tags after they are attached to products. The retailer may further mandate that the distribution center 112 should test 1% of the RFID tags upon receipt of the products from the retail vendor/supplier 110, and the retail store 114 should test 0.5% of the RFID tags upon receipt of the products from the distribution center 112. The analytic data from the data analysis engine 204 may then be utilized by the end user 118 to ensure that the required scan activity is occurring and to determine if compliance was not met by particular entities in the supply chain 101.

A failure prediction module 206 may be in communication with the RFID tag data database 208 and/or the data analysis engine 204 to predict failures of other RFID tags that will be in the supply chain 101 in the future, based on the analytic data. In particular, the analytic data is based on RFID tags that are progressing or have already progressed through the supply chain 101, and therefore can be used to predict potential failures of RFID tags that will progress through the supply chain 101 in the future. The failure prediction module 206 can alert the end user 118 that a significant number of RFID tags are defective, or are likely to become defective, at a certain point in the supply chain 101 and/or alert the end user 118 of other information related to defective RFID tags. The end user 118 may utilize the alert and/or information to take certain actions to minimize the occurrence of defective RFID tags. For example, if defective or underperforming RFID tags are scanned at a certain point in the supply chain 101, the failure prediction module 206 can alert the end user 118 of this issue. The end user 118 could request that additional scans of RFID tags take place at this point in the supply chain 101 for quality control purposes to determine whether particular RFID tags are more prone to failure, such as RFID tags of a certain inlay lot number, tag printer/converter lot number, at a particular location of a retail vendor/supplier 110, etc.

An RFID tag validation module 210 can be in communication with the tag printer/converter 108, the retail vendor/supplier 110, the distribution center 112, the retail store 114, the inlay manufacturer 106, and/or the retailer 250 to validate inlay-SKU combinations of RFID tags in the supply chain 101. In embodiments, the RFID tag validation module 210 may also be used to detect a duplicate SGTIN in multiple RFID tags, and/or verify whether a SGTIN in an RFID tag conforms to a specified encoding scheme, as described above.

As previously discussed, an inlay includes an RFID chip attached to an antenna. In some situations, a retailer 250 may specify a particular combination of antenna and RFID chip be used for particular products or categories of products. For example, a larger antenna may be required for certain products so that the inlay within the RFID tag can be read from a farther distance. In embodiments, when an RFID tag is finished at a tag printer/converter 108, the tag printer/converter 108 can request the RFID tag validation module 210 to validate that the proper inlay-SKU combination is being used in the RFID tag. In other embodiments, the retail vendor/supplier 110, distribution center 112, and/or the retail store 114 can request the RFID tag validation module 210 to validate that the proper inlay-SKU combination is being used in the RFID tag. In particular, the RFID tag validation module 210 can utilize information from the inlay manufacturer 106 and the retailer 250 to determine if a finished RFID tag includes the proper inlay corresponding to the SKU of the product the RFID tag is intended for. In this way, it can be determined whether authorized or unauthorized RFID chips have been used in particular inlays and/or RFID tags.

The information from the inlay manufacturer 106 may include the TID of the RFID chip and the inlay model number, and can be received by the RFID tag validation module 210 and/or stored in the inlay data database 212. In some embodiments, the information may be transmitted from the inlay manufacturer 106 in response to queries by the RFID tag validation module 210, in addition to or instead of storing the information in the inlay data database 212. A particular RFID chip may have been attached to an antenna of the inlay corresponding to the particular inlay model number. In this way, the RFID tag validation module 210 can associate each unique TID of an RFID chip with an inlay model, and store this association in the inlay data database 212. The retailer 250 can transmit product category data, SKU data, and specified inlay data to the RFID tag validation module 210, and store this information in the retailer data database 214. In some embodiments, the product category data, SKU data, and specified inlay data may be transmitted from the retailer 250 in response to queries by the RFID tag validation module 210, in addition to or instead of storing this data in the retailer data database 214. The SKU data may specify the particular SKUs that are to be used for a certain product or product category, and the specified inlay data may indicate the particular inlays that are to be used with the certain product or product category.

When the tag printer/converter 108 finishes an RFID tag or the retail vendor/suppler 110, distribution center 112, and/or retail store 114 scans an RFID tag, the entity can request that the RFID tag validation module 210 validate that the proper inlay-SKU combination is being used in the RFID tag. The request can include the SKU of the product and the read TID of the RFID chip in the RFID tag that was finished. In some embodiments, the SKU of the product (that is included in the request) may be derived from the SGTIN in the scanned RFID tag. The RFID tag validation module 210 can then utilize the TID of the RFID chip, the inlay model number, product category data, SKU data, specified inlay data, the SKU of the product, and the read TID to determine if the inlay-SKU combination of the RFID tag is valid. In particular, the read TID can be matched to the TID stored in the inlay data database 212 to determine the associated inlay model number, and the SKU can be matched to the SKU data in the retailer data database 214 to determine the product category at issue. If the associated inlay model number matches the specified inlay data for the product category the RFID tag is being made for, then the inlay-SKU combination may be deemed valid. An inlay-SKU combination validated message can be transmitted to the requesting entity from the RFID tag validation module 210 in this case. However, if the associated inlay model number does not match the specified inlay data for the product category the RFID tag is being made for, then the inlay-SKU combination may be deemed invalid and an inlay-SKU combination validation error may be transmitted to the requesting entity from the RFID tag validation module 210. In some embodiments, even if the inlay-SKU combination is deemed valid (i.e., the RFID tag is valid and has the correct inlay), a human-readable SKU printed on a UPC barcode on the RFID tag can be entered by a user to determine whether the RFID tag is attached to the correct product.

FIG. 3 is a block diagram of a computing device 300 housing executable software used to facilitate the RFID measurement and tracking system 102. One or more instances of the computing device 300 may be utilized to implement any, some, or all of the components in the system 102, including the RFID tag scan data collection module 202, the data analysis engine 204, the quality control process module 205, the failure prediction module 206, and the RFID tag validation module 210. Computing device 300 includes a memory element 304. Memory element 304 may include a computer readable medium for implementing the system 102, and for implementing particular system transactions. Memory element 304 may also be utilized to implement the RFID tag data database 208, the inlay data database 212, and the retailer data database 214. Computing device 300 also contains executable software, some of which may or may not be unique to the system 102.

In some embodiments, the system 102 is implemented in software, as an executable program, and is executed by one or more special or general purpose digital computer(s), such as a mainframe computer, a personal computer (desktop, laptop or otherwise), personal digital assistant, or other handheld computing device. Therefore, computing device 300 may be representative of any computer in which the system 102 resides or partially resides.

Generally, in terms of hardware architecture as shown in FIG. 3, computing device 300 includes a processor 302, a memory 304, and one or more input and/or output (I/O) devices 306 (or peripherals) that are communicatively coupled via a local interface 308. Local interface 308 may be one or more buses or other wired or wireless connections, as is known in the art. Local interface 308 may have additional elements, which are omitted for simplicity, such as controllers, buffers (caches), drivers, transmitters, and receivers to facilitate external communications with other like or dissimilar computing devices. Further, local interface 308 may include address, control, and/or data connections to enable internal communications among the other computer components.

Processor 302 is a hardware device for executing software, particularly software stored in memory 304. Processor 302 can be any custom made or commercially available processor, such as, for example, a Core series or vPro processor made by Intel Corporation, or a Phenom, Athlon or Sempron processor made by Advanced Micro Devices, Inc. In the case where computing device 300 is a server, the processor may be, for example, a Xeon or Itanium processor from Intel, or an Opteron-series processor from Advanced Micro Devices, Inc. Processor 302 may also represent multiple parallel or distributed processors working in unison.

Memory 304 can include any one or a combination of volatile memory elements (e.g., random access memory (RAM, such as DRAM, SRAM, SDRAM, etc.)) and non-volatile memory elements (e.g., ROM, hard drive, flash drive, CDROM, etc.). It may incorporate electronic, magnetic, optical, and/or other types of storage media. Memory 304 can have a distributed architecture where various components are situated remote from one another, but are still accessed by processor 302. These other components may reside on devices located elsewhere on a network or in a cloud arrangement.

The software in memory 304 may include one or more separate programs. The separate programs comprise ordered listings of executable instructions for implementing logical functions. In the example of FIG. 3, the software in memory 304 may include the system 102 in accordance with the invention, and a suitable operating system (O/S) 312. Examples of suitable commercially available operating systems 312 are Windows operating systems available from Microsoft Corporation, Mac OS X available from Apple Computer, Inc., a Unix operating system from AT&T, or a Unix-derivative such as BSD or Linux. The operating system O/S 312 will depend on the type of computing device 300. For example, if the computing device 300 is a PDA or handheld computer, the operating system 312 may be iOS for operating certain devices from Apple Computer, Inc., PalmOS for devices from Palm Computing, Inc., Windows Phone 8 from Microsoft Corporation, Android from Google, Inc., or Symbian from Nokia Corporation. Operating system 312 essentially controls the execution of other computer programs, such as the system 102, and provides scheduling, input-output control, file and data management, memory management, and communication control and related services.

If computing device 300 is an IBM PC compatible computer or the like, the software in memory 304 may further include a basic input output system (BIOS). The BIOS is a set of essential software routines that initialize and test hardware at startup, start operating system 312, and support the transfer of data among the hardware devices. The BIOS is stored in ROM so that the BIOS can be executed when computing device 300 is activated.

Steps and/or elements, and/or portions thereof of the invention may be implemented using a source program, executable program (object code), script, or any other entity comprising a set of instructions to be performed. Furthermore, the software embodying the invention can be written as (a) an object oriented programming language, which has classes of data and methods, or (b) a procedural programming language, which has routines, subroutines, and/or functions, for example but not limited to, C, C++, C#, Pascal, Basic, Fortran, Cobol, Perl, Java, Ada, Python, and Lua. Components of the system 102 may also be written in a proprietary language developed to interact with these known languages.

I/O device 306 may include input devices such as a keyboard, a mouse, a scanner, a microphone, a touch screen, a bar code reader, or an infra-red reader. It may also include output devices such as a printer, a video display, an audio speaker or headphone port or a projector. I/O device 306 may also comprise devices that communicate with inputs or outputs, such as a short-range transceiver (RFID, Bluetooth, etc.), a telephonic interface, a cellular communication port, a router, or other types of network communication equipment. I/O device 306 may be internal to computing device 300, or may be external and connected wirelessly or via connection cable, such as through a universal serial bus port.

When computing device 300 is in operation, processor 302 is configured to execute software stored within memory 304, to communicate data to and from memory 304, and to generally control operations of computing device 300 pursuant to the software. The system 102 and operating system 312, in whole or in part, may be read by processor 302, buffered within processor 302, and then executed.

In the context of this document, a "computer-readable medium" may be any means that can store, communicate, propagate, or transport data objects for use by or in connection with the system 102. The computer readable medium may be for example, an electronic, magnetic, optical, electromagnetic, infrared, or semiconductor system, apparatus, device, propagation medium, or any other device with similar functionality. More specific examples (a non-exhaustive list) of the computer-readable medium would include the following: an electrical connection (electronic) having one or more wires, a random access memory (RAM) (electronic), a read-only memory (ROM) (electronic), an erasable programmable read-only memory (EPROM, EEPROM, or Flash memory) (electronic), an optical fiber (optical), and a portable compact disc read-only memory (CDROM) (optical). Note that the computer-readable medium could even be paper or another suitable medium upon which the program is printed, as the program can be electronically captured, via, for instance, optical scanning of the paper or other medium, then compiled, interpreted or otherwise processed in a suitable manner if necessary, and stored in a computer memory. The system 102 can be embodied in any type of computer-readable medium for use by or in connection with an instruction execution system or apparatus, such as a computer.

For purposes of connecting to other computing devices, computing device 300 is equipped with network communication equipment and circuitry. In a preferred embodiment, the network communication equipment includes a network card such as an Ethernet card, or a wireless connection card. In a preferred network environment, each of the plurality of computing devices 300 on the network is configured to use the Internet protocol suite (TCP/IP) to communicate with one another. It will be understood, however, that a variety of network protocols could also be employed, such as IEEE 802.11 Wi-Fi, address resolution protocol ARP, spanning-tree protocol STP, or fiber-distributed data interface FDDI. It will also be understood that while a preferred embodiment of the invention is for each computing device 300 to have a broadband or wireless connection to the Internet (such as DSL, Cable, Wireless, T-1, T-3, OC3 or satellite, etc.), the principles of the invention are also practicable with a dialup connection through a standard modem or other connection means. Wireless network connections are also contemplated, such as wireless Ethernet, satellite, infrared, radio frequency, Bluetooth, near field communication, and cellular networks.

Figure 4:
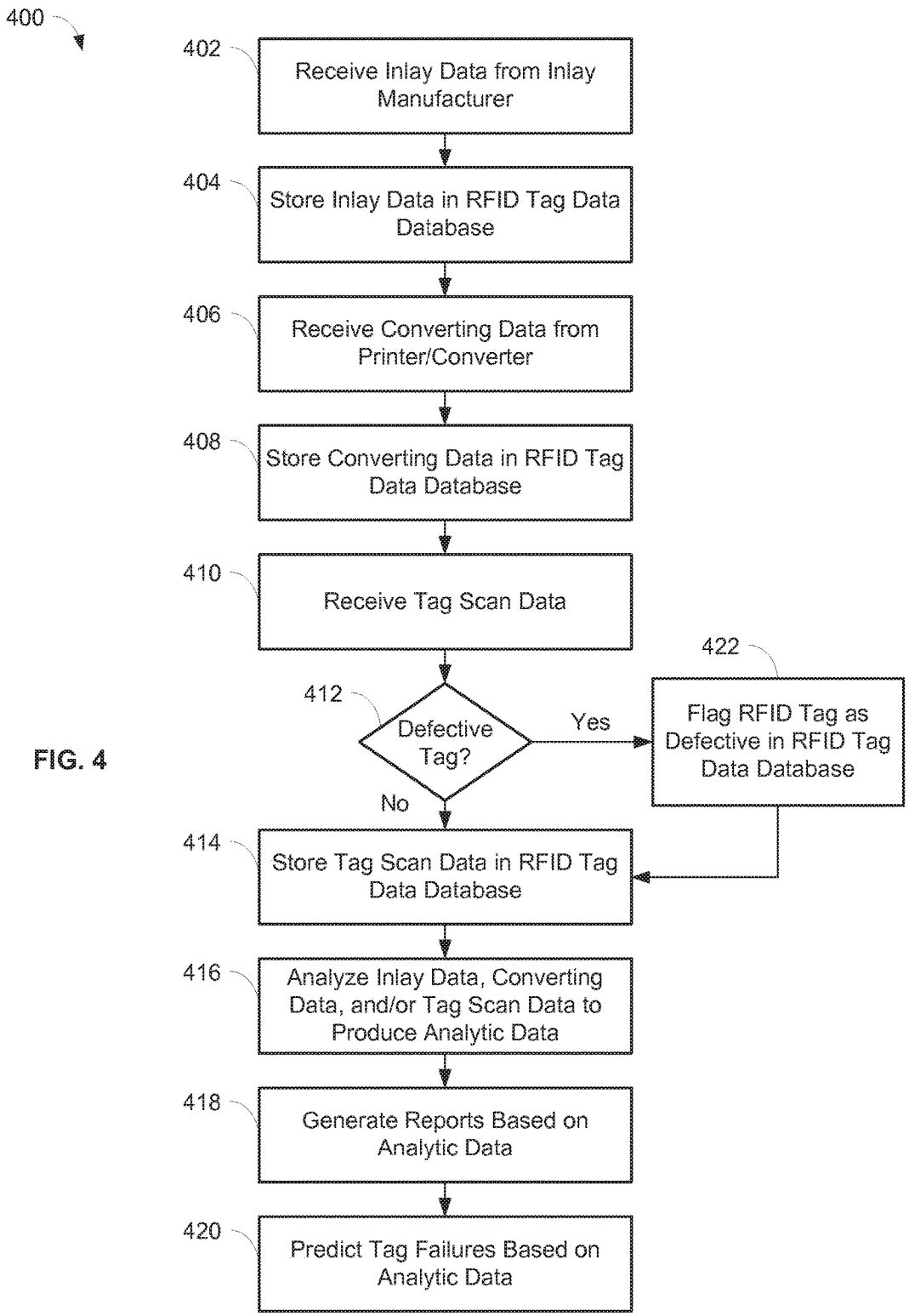
FIG. 4 is a flowchart illustrating operations for measuring and tracking RFID tag performance across the supply chain.

An embodiment of a process 400 for measuring and tracking RFID tag performance across a supply chain is shown in FIG. 4. The process 400 can result in the determination of defective or underperforming RFID tags based on tag scan data, flagging defective RFID tags in a database, storing the tag scan data in the database to ensure quality control metrics are met, producing analytic data related to the RFID tags, and/or predicting failures of RFID tags in the supply chain. End users utilizing the process 400 can obtain more accurate inventory data, reduce costs related to tagging and re-tagging of products with RFID tags, and/or be assisted in complying with various quality control requirements related to the RFID tags.

At step 402, inlay data may be received from an inlay manufacturer. The inlay data may include the manufacture date, lot number, antenna type, inlay model number, the quality control test results, the TID of the RFID chip in the RFID tag, and/or other data related to a produced inlay intended for use in an RFID tag. The inlay data may be stored at step 404 in an RFID tag data database. At step 406, converting data may be received from a tag printer/converter. The converting data may include a date and/or timestamp when the RFID tag was encoded, an order number, vendor(s) the RFID tag was shipped to, and/or other information. The converting data may be stored at step 408 in the RFID tag data database. In some embodiments, the inlay data and/or converting data may be transmitted from the inlay manufacturer and/or the tag printer/converter at steps 402 and 406, respectively, in response to queries, in addition to or instead of storing the inlay data and/or converting data in the RFID tag data database at steps 404 and 408, respectively. For example, information from the tag scan data, e.g., TID of an RFID chip in a scanned RFID tag, received at step 410 may be included in such queries.

As RFID tags are conveyed in the supply chain, tag scan data may be received at step 410 from entities in the supply chain. The tag scan data may include the SGTIN of an RFID tag, the TID of the RFID chip in the RFID tag, a tag grade, a date and/or timestamp when the RFID tag was scanned, a location of the scan, a user who performed the scan, performance data, and/or other information. The SKU of a product may be derived from the SGTIN of the RFID tag in the tag scan data. At step 412, it may be determined whether the RFID tag associated with the received tag scan data is defective, based on the tag scan data. For example, an RFID tag may be determined to be defective at step 412 if a secondary barcode was manually entered instead of receiving an RFID scanned SGTIN. An RFID tag may also be determined to be defective at step 412 if a duplicate SGTIN is detected in multiple RFID tags having unique TIDs, and/or if the SGTIN for an RFID tag does not conform to a specified encoding scheme.

If the RFID tag at issue is determined to be defective at step 412, then the process 400 may continue to step 422. At step 422, the RFID tag at issue may be flagged as defective in the RFID tag data database, and other information may also be stored, such as a timestamp, the SGTIN of the RFID tag, geoposition where the scan took place, an identifier of the device which was used to scan the RFID tag, an operator name, and/or other information. Flagging the RFID tag as defective at step 422 may also include transmitting a message with information related to the defective RFID tag. The process 400 may continue to step 414 following step 422 to store other tag scan data received at step 410 in the RFID tag data database.

However, if the RFID tag at issue is determined to not be defective at step 412, then the process 400 may also continue to step 414 and the tag scan data received at step 410 may be stored in the RFID tag data database. At step 416, the inlay data, the converting data, and/or the tag scan data may be analyzed to produce analytic data related to the RFID tags. The analytic data may be utilized to determine causes of RFID tag failure, generate the history of RFID tags, and/or for other purposes. The analysis performed at step 416 may be based on none, some, or all of the inlay data; none, some, or all of the converting data; and/or none, some, or all of the tag scan data. The analytic data may be generated and provided as reports in a text format, XML format, HTML format, and/or other appropriate format, for example, at step 418. The analytic data and/or the tag scan data may also be utilized to ensure that quality control metrics are met. At step 420, failures of RFID tags used in the supply chain in the future can be predicted based on the analytic data. For example, an end user can be alerted at step 420 that a significant number of RFID tags are defective at a certain point in the supply chain. The end user may utilize the alert and/or other information to take certain actions to minimize the occurrence of defective RFID tags.

Figure 5:
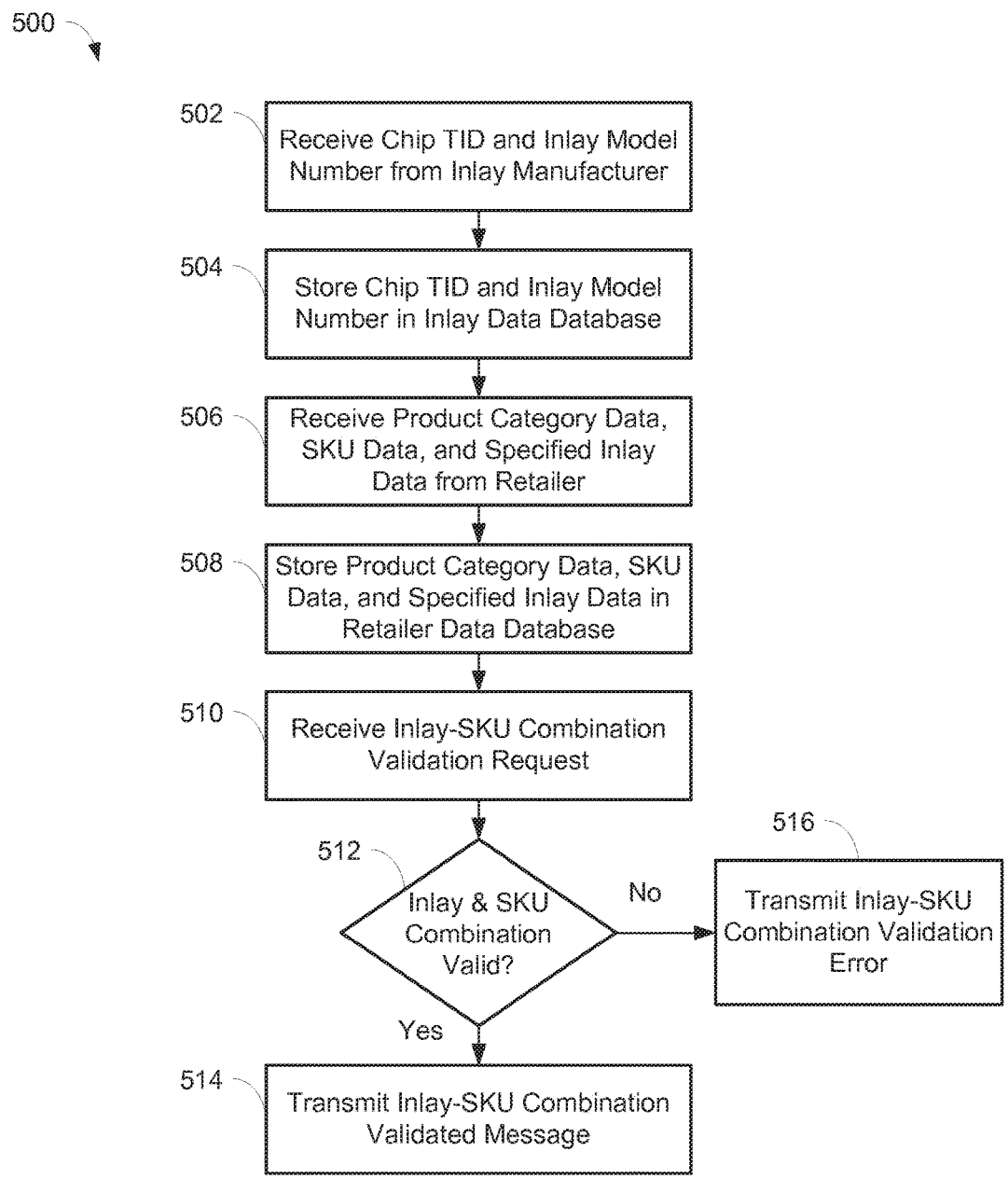
FIG. 5 is a flowchart illustrating operations for validating inlay-SKU combinations of RFID tags within the supply chain.

An embodiment of a process 500 for validating inlay-SKU combinations of RFID tags in a supply chain is shown in FIG. 5. The process 500 may result in validating that a particular RFID tag is utilizing the correct inlay (i.e., RFID chip and antenna) for the SKU and product the RFID tag will be attached to. A retailer may have specified that certain inlays be used in RFID tags for particular products for performance reasons, for example. In this way, the wrong inlays will not be included in RFID tags for those products and costs can be reduced so that such products do not have to be retagged with RFID tags that have the correct inlays.

At step 502, a TID of an RFID chip and an inlay model number may be received from an inlay manufacturer. A particular RFID chip may have been attached to an antenna of the inlay corresponding to the particular inlay model number. The TID of the RFID chip and the inlay model number may be stored at step 504 in an inlay data database. At step 506, product category data, SKU data, and specified inlay data may be received from a retailer. The SKU data may specify the particular SKUs that are to be used for a certain product or product category, and the specified inlay data may indicate the particular inlays that are to be used with the certain product or product category. The product category data, SKU data, and specified inlay data may be stored at step 508 in a retailer data database. In some embodiments, the information may be transmitted from the inlay manufacturer at step 502 in response to queries, in addition to or instead of storing the information in the inlay data database at step 504. Similarly, in some embodiments, the product category data, SKU data, and specified inlay data may be transmitted from the retailer at step 506 in response to queries, in addition to or instead of storing this data in the retailer data database at step 508.

At step 510, an inlay-SKU combination validation request can be received from a tag printer/converter, retail vendor/supplier, distribution center, and/or retail store. The inlay-SKU combination validation request may be for validating that the proper inlay-SKU combination is being used in a particular RFID tag, and may include the SKU of the product and the read TID of the RFID chip in the RFID tag that was finished by the tag printer/converter. In some embodiments, the SKU of the product (that is included in the request) may be derived from the SGTIN in the scanned RFID tag. It may be determined at step 512 whether the inlay and SKU combination is valid. The TID of the RFID chip, the inlay model number, product category data, SKU data, specified inlay data, the SKU of the product, and the read TID can be used at step 512 to determine if the inlay-SKU combination of the RFID tag is valid. In particular, the read TID can be matched to the TID stored in the inlay data database to determine the associated inlay model number, and the SKU can be matched to the SKU data in the retailer data database to determine the product category at issue. If the associated inlay model number matches the specified inlay data for the product category the RFID tag is being made for at step 512, then the inlay-SKU combination may be deemed valid. An inlay-SKU combination validated message can be transmitted at step 514 to the requesting entity in this case. However, if the associated inlay model number does not match the specified inlay data for the product category the RFID tag is being made for at step 512, then the inlay-SKU combination may be deemed invalid and an inlay-SKU combination validation error may be transmitted at step 516 to the requesting entity.

According to an exemplary implementation, the systems and methods described herein can be applied in an auditing and compliance process in connection with licensing and/or other tracking requirements associated with RFID chips within RFID tags, such as inlays that consist of RFID chips attached to antennas. Information that may be retrieved from an RFID tag may include the TID of an RFID chip, the SGTIN, the manufacturer of the RFID chip, and/or other information. Such information may be obtained by scanning the RFID tag. The scanning may be performed, for example, by a chip manufacturer 104, an inlay manufacturer 106, an RFID tag printer/converter 108, a retail vendor/supplier 110, a distribution center 112, a retail store 114, and/or an end user 118. The end user 118 may include, for example, an auditor, a compliance entity, and/or any other user that may have a need to access the information. In some embodiments, the RFID tag may be scanned by the RFID inlay rating device 116. Tag scan data, as described previously, may be received as a result of the scanning of the RFID tag.

The RFID measurement and tracking system 102 can use the tag scan data to determine whether certain functions, capabilities, and/or particular versions of an inlay and/or an RFID chip are present. In some instances, it may be desirable to determine whether a particular inlay is used in an RFID tag, whether a particular version of an RFID chip is being used in an inlay, and/or whether a particular function or capability is present in an inlay and/or the RFID chip. In other instances, it may be desirable to make such determinations in connection with a license. For example, the systems and methods described herein can be used to determine whether particular inlays and/or RFID chips are licensed or unlicensed, as illustrated in the process 600 shown in FIG. 6.

Figure 6:
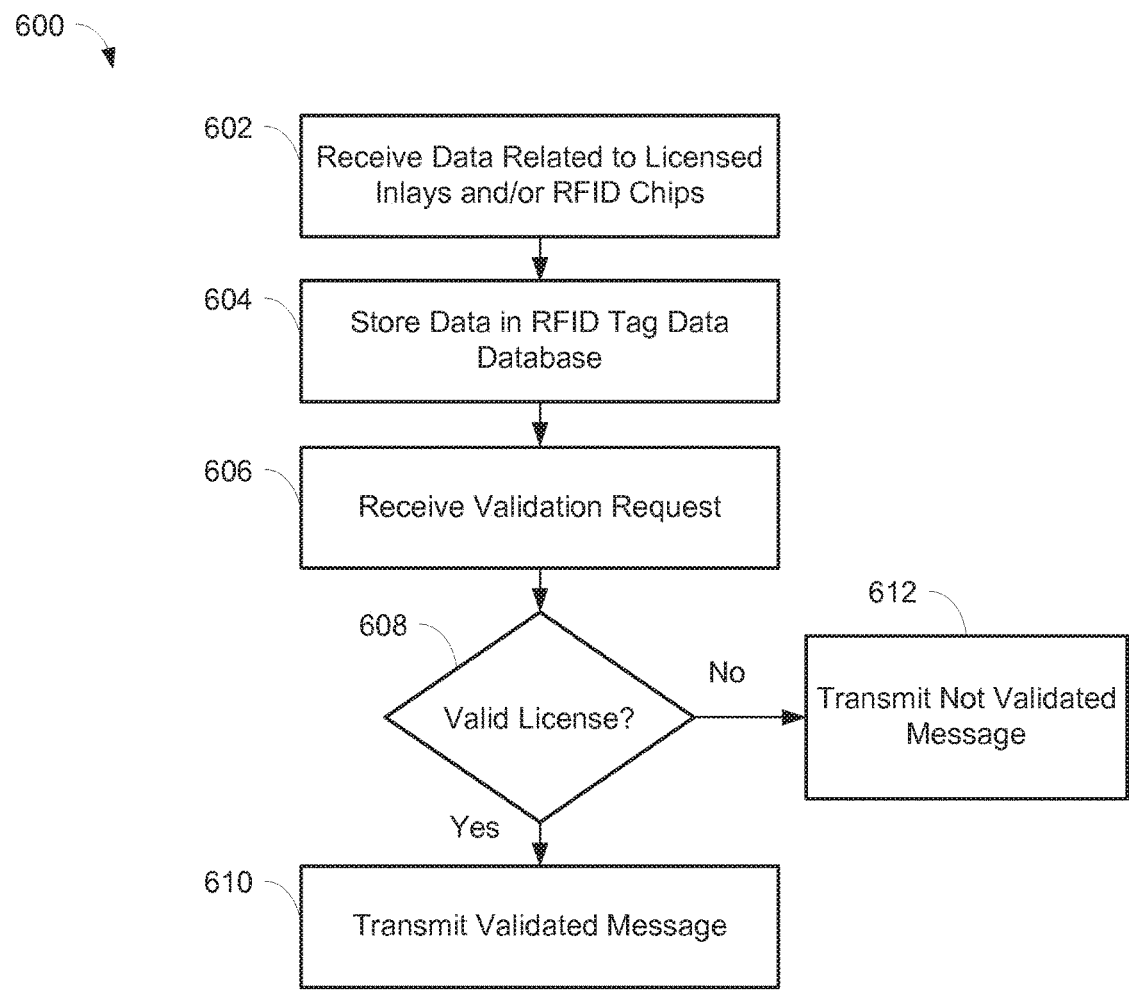
FIG. 6 is a flowchart illustrating operations for validating inlays and/of RFID chips in RFID tags for compliance with license agreements.

In the process 600 shown in FIG. 6, data may be received at step 602 and stored in an RFID tag data database at step 604. The data may be associated with inlays and/or RFID chips that have been produced by properly licensed entities, and may include inlay model numbers, the TIDs of RFID chips, manufacture dates, lot numbers, antenna types, and/or other data, e.g., data that can identify the manufacturer or origin of the inlays and/or the RFID chips. At step 606, a validation request may be received from an entity (e.g., end user 118) scanning an RFID tag, for example, to validate that a particular inlay and/or RFID chip in the RFID tag is properly licensed. The validation request may include tag scan data. The tag scan data, as described previously, may be obtained by an RFID tag reader, the RFID inlay rating device 116, and/or other devices, for example. It may be determined at step 608 whether the inlay and/or RFID chip associated with the validation request has a valid license, such as by comparing the tag scan data with the data previously stored in the RFID tag data database at step 602.

For example, in one embodiment, when an RFID tag is scanned, the RFID measurement and tracking system 102 can determine whether the producer of an inlay is a party to a license agreement, based on comparing the tag scan data to the previously stored data. In another embodiment, the RFID measurement and tracking system 102 can determine whether the manufacturer of an RFID chip is party to a license agreement, based on comparing the tag scan data to the previously stored data. In a further embodiment, the RFID measurement and tracking system 102 can use the tag scan data to determine whether the functions, capabilities, and/or version of the inlay and/or RFID chip are compliant with a license agreement. If the inlay and/or RFID chip has a valid license at step 608, then a validated message may be transmitted at step 610. If the inlay and/or RFID chip does not have a valid license at step 610, then a not validated message may be transmitted at step 612. For example, the messages at steps 610 and/or 612 can be transmitted to the entity that made the validation request at step 606. In some embodiments, the validated message and not validated message may be transmitted to a device (e.g., an RFID inlay rating device 116) so that a user can immediately be informed whether a scanned inlay and/or RFID chip of a particular RFID tag is licensed or unlicensed. At steps 610 and 612, in addition to or in lieu or transmitting the messages, the inlay and/or RFID chip may be flagged or marked in a database, e.g., the RFID tag data database 208, as having been validated for proper licensing and with the results of the validation. Determining whether an inlay and/or RFID chip is licensed or unlicensed can assist a licensor, a licensee, and/or other entities with the auditing and compliance related to a license agreement. The data analysis engine 204, for example, may be utilized to implement such auditing and compliance.

Figure 7:
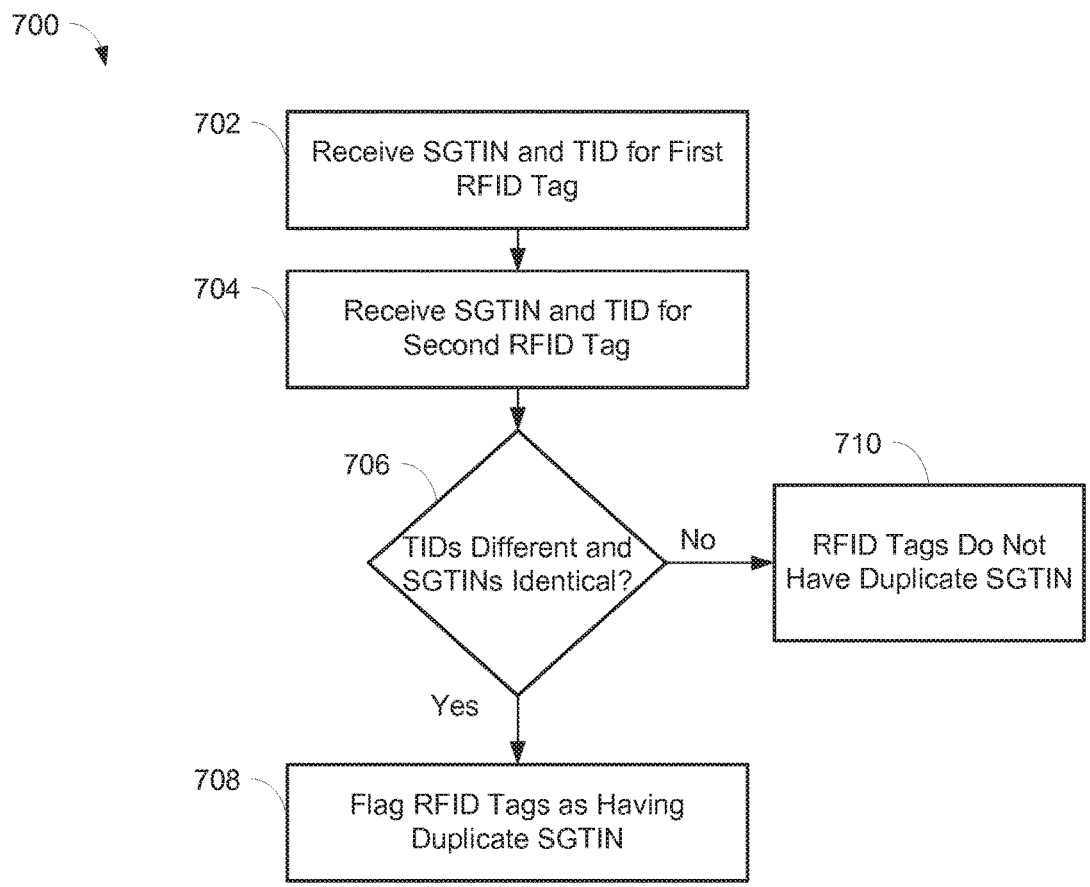
FIG. 7 is a flowchart illustrating operations for detecting a duplicate SGTIN encoded in a plurality of RFID tags.

FIG. 7 is a flowchart of a process 700 for detecting a duplicate SGTIN encoded in a plurality of RFID tags. If an SGTIN is encoded in multiple RFID tags, the RFID tags can be considered defective because each RFID tag should have a unique SGTIN. Incorrect inventory counts of products can result when there is a duplicate SGTIN encoded in multiple RFID tags because a scanner will only detect the presence of the single SGTIN and believe that there is only one corresponding product. Tag scan data can be received at steps 702 and 704 of the process 400, and may include the scanned SGTINs and TIDs from multiple RFID tags. The TIDs are uniquely encoded in each RFID chip in the RFID tags by a chip manufacturer. Other information may also be received with the tag scan data at steps 702 and 704, as described previously.

At step 706, it can be determined whether the received TIDs are different and the received SGTINs are identical. If it is determined that the TIDs are different and the SGTINs are identical, then the process 700 can continue to step 708 and flag the RFID tags as defective for having a duplicate SGTIN. The RFID tags can be flagged as defective in a database, and/or a message can be transmitted indicating that the RFID tags have a duplicate SGTIN. Other information from the tag scan data may also be stored in the database and/or transmitted in the message. However, if it is determined at step 706 that the TIDs are different and the SGTINs are not identical, then the process 700 can continue to step 710. At step 710, a message can be transmitted that the RFID tags do not have a duplicate SGTIN, the RFID tags can be indicated as not having a duplicate SGTIN in a database, and/or no action may occur.

Figure 8:
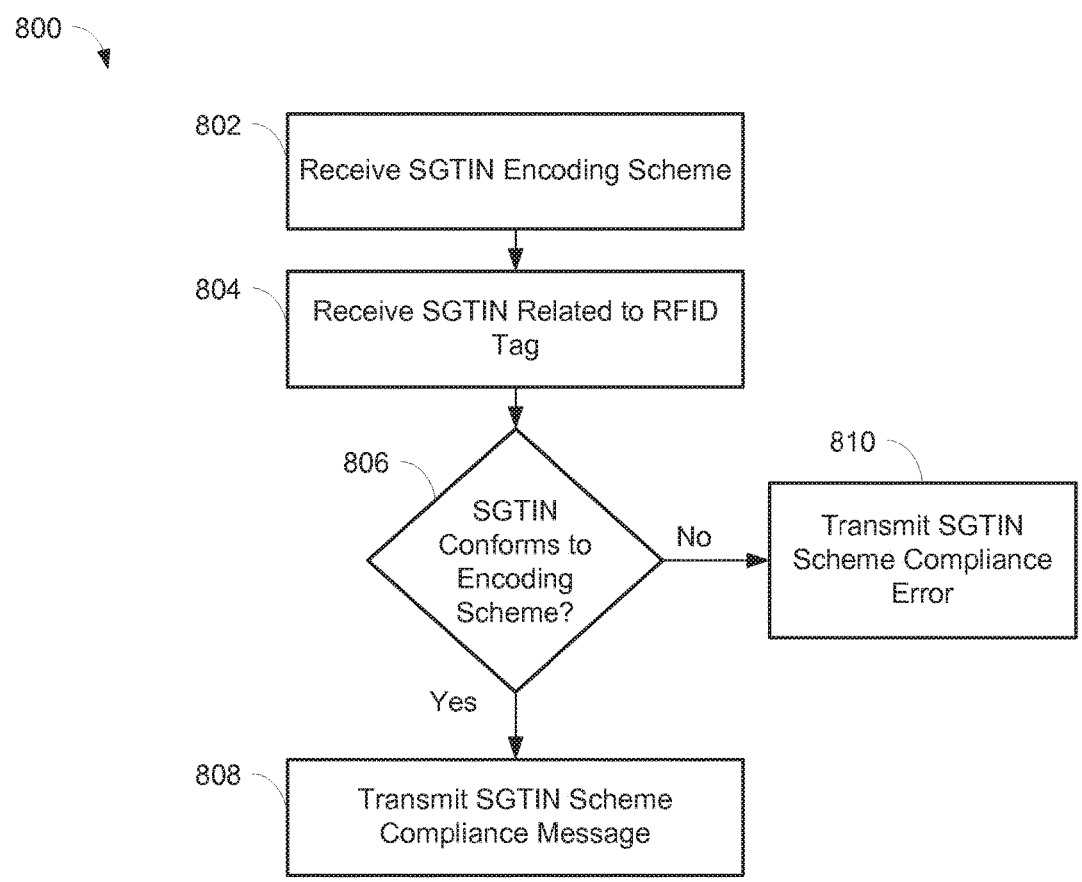
FIG. 8 is a flowchart illustrating operations for verifying compliance of an SGTIN with an encoding scheme.

FIG. 8 is a flowchart of a process 800 for verifying compliance of an SGTIN with an encoding scheme. If the SGTIN for a particular RFID tag does not conform to a specified encoding scheme, then the RFID tag can be considered defective. The encoding scheme may specify the format of the SGTIN based on a SKU and a serial number related to a product. A retailer may specify a proprietary encoding scheme, for example, and/or the encoding scheme may be a standardized scheme. Proper use of the encoding scheme will minimize the possibility of encoding a duplicate SGTIN in multiple RFID tags. At step 802, an SGTIN encoding scheme can be received, and may include, for example, rules that ensure the unique combination of the SKU and the serial number to form an SGTIN. Tag scan data can be received at step 804, and may include the scanned SGTIN from an RFID tag. Other information may also be received with the tag scan data at steps 804, as described previously.

At step 806, it can be determined whether the received SGTIN conforms to the encoding scheme. For example, the SGTIN can be compared to the rules of the encoding scheme to ensure that the SGTIN was formatted properly. If it is determined that the SGTIN conforms to the encoding scheme, then the process 800 can continue to step 808 and transmit an SGTIN scheme compliance message. The RFID tag can also be flagged in a database at step 808 to indicate that its SGTIN conforms to the encoding scheme. However, if it is determined at step 806 that the SGTIN does not conform to the encoding scheme, then the process 800 can continue to step 810. At step 810, an SGTIN scheme compliance error can be transmitted. The RFID tag can also be flagged in a database at step 810 to indicate that its SGTIN does not conform to the encoding scheme. Other information from the tag scan data may also be stored in the database and/or transmitted in the message or error at step 808 and/or 810.

Any process descriptions or blocks in figures should be understood as representing modules, segments, or portions of code which include one or more executable instructions for implementing specific logical functions or steps in the process, and alternate implementations are included within the scope of the embodiments of the invention in which functions may be executed out of order from that shown or discussed, including substantially concurrently or in reverse order, depending on the functionality involved, as would be understood by those having ordinary skill in the art.

It should be emphasized that the above-described embodiments of the invention, particularly, any "preferred" embodiments, are possible examples of implementations, merely set forth for a clear understanding of the principles of the invention. Many variations and modifications may be made to the above-described embodiment(s) of the invention without substantially departing from the spirit and principles of the invention. All such modifications are intended to be included herein within the scope of this disclosure and the invention and protected by the following claims.

The invention claimed is:

1. A method for measuring a plurality of radio-frequency identification (RFID) tags, using a processor, the method comprising:
   receiving tag scan data related to at least one RFID tag of the plurality of RFID tags at the processor, wherein the tag scan data comprises a unique identifier of the at least one RFID tag;
   receiving inlay data at the processor, the inlay data related to a plurality of inlays each comprising an RFID chip and an antenna, wherein the plurality of inlays is used in producing the plurality of RFID tags;
   receiving converting data at the processor, the converting data related to the plurality of RFID tags after the plurality of RFID tags have been finished, wherein each of the plurality of RFID tags comprises one of the plurality of inlays;
   determining whether the tag scan data denotes that the at least one RFID tag is defective, based on one or more of the tag scan data, the inlay data, or the converting data, using the processor; and
   flagging the at least one RFID tag as defective in an RFID tag data database, using the processor, if the tag scan data denotes that the at least one RFID tag is defective, by storing in the RFID tag data database the unique identifier of the at least one RFID tag.

2. The method of claim 1, wherein flagging the at least one RFID tag as defective comprises flagging the at least one RFID tag as defective in the RFID tag data database, using the processor, if the tag scan data denotes that the at least one RFID tag is defective, by storing in the RFID tag data database one or more of the unique identifier of the at least one RFID tag, a timestamp when the at least one RFID tag was scanned, a location of the scan, an identifier of a device which was used to scan the at least one RFID tag, or an operator name who performed the scan.

3. The method of claim 1, wherein determining whether the tag scan data denotes that the at least one RFID tag is defective comprises determining that the at least one RFID tag is defective, using the processor, if the tag scan data comprises manually-inputted information instead of the unique identifier of the at least one RFID tag.

4. The method of claim 1, wherein:
the tag scan data comprises a first unique identifier and a first Tag Identification Number (TID) related to a first RFID tag of the plurality of RFID tags, and a second unique identifier and a second TID related to a second RFID tag of the plurality of RFID tags; and
determining whether the tag scan data denotes that the at least one RFID tag is defective comprises determining whether the first TID and the second TID are different and the first unique identifier and the second unique identifier are identical, using the processor; and
flagging the at least one RFID tag as defective in the RFID tag data database comprises flagging the first and second RFID tags as having a duplicate unique identifier in the RFID tag data database, using the processor, if the first TID and the second TID are different and the first unique identifier and the second unique identifier are identical.

5. The method of claim 1, wherein:
the tag scan data further comprises payload data of the at least one RFID tag;
determining whether the tag scan data denotes that the at least one RFID tag is defective comprises determining whether one or more of the unique identifier or the payload data conforms to an encoding scheme; and
flagging the at least one RFID tag as defective in the RFID tag data database comprises flagging the at least one RFID tag as not complying with the encoding scheme, if one or more of the unique identifier or the payload data is determined as not conforming to the encoding scheme.

6. The method of claim 1, wherein:
the tag scan data further comprises payload data of the at least one RFID tag;
determining whether the tag scan data denotes that the at least one RFID tag is defective comprises determining whether an inlay-payload data combination is valid; and
flagging the at least one RFID tag as defective in the RFID tag data database comprises flagging the inlay-payload data combination of the at least one RFID tag as invalid, if the inlay and the payload data do not correspond to one another.

7. The method of claim 1, further comprising:
producing analytic data based on one or more of the tag scan data, the inlay data, or the converting data, using the processor, the analytic data related to the plurality of RFID tags; and
transmitting the analytic data from the processor.

8. The method of claim 7, further comprising:
predicting one or more failures of a second plurality of RFID tags, based on the analytic data;
generating failure prediction information based on the prediction of the one or more failures, using the processor; and
transmitting the failure prediction information from the processor.

9. The method of claim 8, further comprising:
generating predicted compliant tag information based on the prediction of the one or more failures, using the processor, wherein the predicted compliant tag information denotes one or more non-failures of the second plurality of RFID tags; and
transmitting the predicted compliant tag information from the processor.

10. The method of claim 1, further comprising:
determining a level of degradation of the at least one RFID tag, based on one or more of the tag scan data, the inlay data, or the converting data, using the processor; and
storing the level of degradation of the at least one RFID tag in the RFID tag data database, using the processor.

11. A method for measuring a plurality of radio-frequency identification (RFID) tags, using a processor, the method comprising:
receiving tag scan data related to at least one RFID tag of the plurality of RFID tags at the processor, wherein the tag scan data comprises a unique identifier of the at least one RFID tag;
receiving inlay data at the processor, the inlay data related to a plurality of inlays each comprising an RFID chip and an antenna, wherein the plurality of inlays is used in producing the plurality of RFID tags;
receiving converting data at the processor, the converting data related to the plurality of RFID tags after the plurality of RFID tags have been finished, wherein each of the plurality of RFID tags comprises one of the plurality of inlays;
determining a level of degradation of the at least one RFID tag, based on one or more of the tag scan data, the inlay data, or the converting data, using the processor; and
storing the level of degradation of the at least one RFID tag in an RFID tag data database, using the processor.

12. The method of claim 11:
wherein the tag scan data further comprises one or more of a timestamp when the at least one RFID tag was scanned, or a location of the scan;
further comprising storing the tag scan data in the RFID tag data database, using the processor.

13. The method of claim 11, further comprising:
producing analytic data based on one or more of the tag scan data, the inlay data, or the converting data, using the processor, the analytic data related to the plurality of RFID tags; and
transmitting the analytic data from the processor.

14. The method of claim 13, further comprising:
predicting one or more failures of a second plurality of RFID tags, based on the analytic data;
generating failure prediction information based on the prediction of the one or more failures, using the processor; and
transmitting the failure prediction information from the processor.

15. The method of claim 14, further comprising:
generating predicted compliant tag information based on the prediction of the one or more failures, using the processor, wherein the predicted compliant tag information denotes one or more non-failures of the second plurality of RFID tags; and
transmitting the predicted compliant tag information from the processor.

16. The method of claim 11, further comprising:
determining whether the tag scan data denotes that the at least one RFID tag is defective, based on one or more of the tag scan data, the inlay data, or the converting data, using the processor; and
flagging the at least one RFID tag as defective in the RFID tag data database, using the processor, if the tag scan data denotes that the at least one RFID tag is defective.

17. The method of claim 16, wherein flagging the at least one RFID tag as defective comprises storing in the RFID tag data database, using the processor, one or more of the unique identifier of the at least one RFID tag, a timestamp when the at least one RFID tag was scanned, a location of the scan, an identifier of a device which was used to scan the at least one RFID tag, or an operator name who performed the scan.

18. A method for measuring a plurality of radio-frequency identification (RFID) tags, using a processor, the method comprising:
- receiving tag scan data related to at least one RFID tag of the plurality of RFID tags at the processor, wherein the tag scan data comprises a unique identifier of the at least one RFID tag;
- receiving inlay data at the processor, the inlay data related to a plurality of inlays each comprising an RFID chip and an antenna, wherein the plurality of inlays is used in producing the plurality of RFID tags;
- receiving converting data at the processor, the converting data related to the plurality of RFID tags after the plurality of RFID tags have been finished, wherein each of the plurality of RFID tags comprises one of the plurality of inlays;
- producing analytic data based on one or more of the tag scan data, the inlay data, or the converting data, using the processor, the analytic data related to the plurality of RFID tags; and
- transmitting the analytic data from the processor.

19. The method of claim 18, further comprising:
- predicting one or more failures of a second plurality of RFID tags, based on the analytic data;
- generating failure prediction information based on the prediction of the one or more failures, using the processor; and
- transmitting the failure prediction information from the processor.

20. The method of claim 19, further comprising:
- generating predicted compliant tag information based on the prediction of the one or more failures, using the processor, wherein the predicted compliant tag information denotes one or more non-failures of the second plurality of RFID tags; and
- transmitting the predicted compliant tag information from the processor.

21. The method of claim 18, further comprising:
- determining whether the tag scan data denotes that the at least one RFID tag is defective, based on one or more of the tag scan data, the inlay data, or the converting data, using the processor; and
- flagging the at least one RFID tag as defective in an RFID tag data database, using the processor, if the tag scan data denotes that the at least one RFID tag is defective.

22. The method of claim 21, wherein flagging the at least one RFID tag as defective comprises storing in the RFID tag data database, using the processor, one or more of the unique identifier of the at least one RFID tag, a timestamp when the at least one RFID tag was scanned, a location of the scan, an identifier of a device which was used to scan the at least one RFID tag, or an operator name who performed the scan.

* * * * *

UNITED STATES PATENT AND TRADEMARK OFFICE
CERTIFICATE OF CORRECTION

PATENT NO. : 9,990,606 B2
APPLICATION NO. : 15/595653
DATED : June 5, 2018
INVENTOR(S) : George Kevin Hoffman Page 1 of 1

It is certified that error appears in the above-identified patent and that said Letters Patent is hereby corrected as shown below:

In the Specification

Column 4, Line 3, "MID tag of the plurality of REED" should be changed to --RFID tag of the plurality of RFID--.

Column 4, Line 11, "measured, inlay" should be changed to --measured. Inlay--.

Signed and Sealed this
Fifteenth Day of January, 2019

Andrei Iancu
*Director of the United States Patent and Trademark Office*